US012637945B2

(12) United States Patent
Tolstaya et al.

(10) Patent No.: US 12,637,945 B2
(45) Date of Patent: May 26, 2026

(54) SYSTEM AND METHOD FOR AUTOMATED DRILL CUTTING MONITORING

(71) Applicant: Saudi Arabian Oil Company, Dhahran (SA)

(72) Inventors: Ekaterina Tolstaya, Moscow (RU); Sergey Safonov, Moscow (RU); Arturo Magana Mora, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 914 days.

(21) Appl. No.: 17/859,561

(22) Filed: Jul. 7, 2022

(65) Prior Publication Data

US 2024/0011393 A1     Jan. 11, 2024

(51) Int. Cl.
| | |
|---|---|
| *E21B 49/00* | (2006.01) |
| *E21B 21/06* | (2006.01) |
| *G01N 33/28* | (2006.01) |
| *G06T 7/00* | (2017.01) |
| *G06T 7/60* | (2017.01) |

(52) U.S. Cl.
CPC .......... *E21B 49/005* (2013.01); *E21B 21/065* (2013.01); *G01N 33/2823* (2013.01); *G06T 7/0004* (2013.01); *G06T 7/60* (2013.01); *G06T 2207/10016* (2013.01); *G06T 2207/30108* (2013.01)

(58) Field of Classification Search
CPC ............................ E21B 49/005; G06T 7/0004
See application file for complete search history.

(56) References Cited

U.S. PATENT DOCUMENTS

| | | | |
|---|---|---|---|
| 891,957 | A | 6/1908 | Schubert |
| 2,110,913 | A | 3/1938 | Lowrey |
| 2,286,673 | A | 6/1942 | Douglas |
| 2,305,062 | A | 12/1942 | Church et al. |
| 2,344,120 | A | 3/1944 | Baker |
| 2,509,608 | A | 5/1950 | Penfield |
| 2,688,369 | A | 9/1954 | Broyles |
| 2,690,897 | A | 10/1954 | Clark |
| 2,719,363 | A | 10/1955 | Richard et al. |
| 2,757,738 | A | 8/1956 | Ritchey |
| 2,795,279 | A | 6/1957 | Erich |

(Continued)

FOREIGN PATENT DOCUMENTS

| | | |
|---|---|---|
| CA | 2537585 | 8/2006 |
| CA | 2669721 | 7/2011 |

(Continued)

OTHER PUBLICATIONS

"Hole Cleaning," Petrowiki, retrieved on Jan. 25, 2019, 8 pages.

(Continued)

*Primary Examiner* — Benjamin O Dulaney
(74) *Attorney, Agent, or Firm* — Dinsmore & Shohl LLP

(57) ABSTRACT

Automated drill cutting monitoring system includes a digital imaging device mounted to a shale shaker of a wellbore drilling assembly and a computer system. The digital imaging device captures digital images of solid objects released when drilling a subterranean zone. The computer system receives the digital images and determines a space occupied by the solid objects on the shale shaker. Using the space occupied by the solid objects on the shale shaker, the computer system determines wellbore conditions.

18 Claims, 4 Drawing Sheets

(56) References Cited

U.S. PATENT DOCUMENTS

| | | | |
|---|---|---|---|
| 2,799,641 A | 7/1957 | Gordon |
| 2,805,045 A | 9/1957 | Goodwin |
| 2,822,150 A | 2/1958 | Muse et al. |
| 2,841,226 A | 7/1958 | Conrad et al. |
| 2,899,000 A | 8/1959 | Medders et al. |
| 2,927,775 A | 3/1960 | Hildebrandt |
| 3,016,244 A | 1/1962 | Friedrich et al. |
| 3,028,915 A | 4/1962 | Jennings |
| 3,087,552 A | 4/1963 | Graham |
| 3,102,599 A | 9/1963 | Hillburn |
| 3,103,975 A | 9/1963 | Hanson |
| 3,104,711 A | 9/1963 | Haagensen |
| 3,114,875 A | 12/1963 | Haagensen |
| 3,133,592 A | 5/1964 | Tomberlin |
| 3,137,347 A | 6/1964 | Parker |
| 3,149,672 A | 9/1964 | Joseph et al. |
| 3,169,577 A | 2/1965 | Erich |
| 3,170,519 A | 2/1965 | Haagensen |
| 3,211,220 A | 10/1965 | Erich |
| 3,220,478 A | 11/1965 | Kinzbach |
| 3,236,307 A | 2/1966 | Brown |
| 3,253,336 A | 5/1966 | Brown |
| 3,268,003 A | 8/1966 | Essary |
| 3,331,439 A | 7/1967 | Lawrence |
| 3,428,125 A | 2/1969 | Parker |
| 3,468,373 A | 9/1969 | Smith |
| 3,522,848 A | 8/1970 | New |
| 3,547,192 A | 12/1970 | Claridge et al. |
| 3,547,193 A | 12/1970 | Gill |
| 3,642,066 A | 2/1972 | Gill |
| 3,656,564 A | 4/1972 | Brown |
| 3,696,866 A | 10/1972 | Dryden |
| 3,839,791 A | 10/1974 | Feamster |
| 3,862,662 A | 1/1975 | Kern |
| 3,874,450 A | 4/1975 | Kern |
| 3,931,856 A | 1/1976 | Barnes |
| 3,946,809 A | 3/1976 | Hagedorn |
| 3,948,319 A | 4/1976 | Pritchett |
| 4,008,762 A | 2/1977 | Fisher et al. |
| 4,010,799 A | 3/1977 | Kern et al. |
| 4,064,211 A | 12/1977 | Wood |
| 4,084,637 A | 4/1978 | Todd |
| 4,135,579 A | 1/1979 | Rowland et al. |
| 4,140,179 A | 2/1979 | Kasevich et al. |
| 4,140,180 A | 2/1979 | Bridges et al. |
| 4,144,935 A | 3/1979 | Bridges et al. |
| 4,191,493 A | 3/1980 | Hansson et al. |
| 4,193,448 A | 3/1980 | Jearnbey |
| 4,193,451 A | 3/1980 | Dauphine |
| 4,196,329 A | 4/1980 | Rowland et al. |
| 4,199,025 A | 4/1980 | Carpenter |
| 4,265,307 A | 5/1981 | Elkins |
| RE30,738 E | 9/1981 | Bridges et al. |
| 4,301,865 A | 11/1981 | Kasevich et al. |
| 4,320,801 A | 3/1982 | Rowland et al. |
| 4,334,928 A | 6/1982 | Hara |
| 4,337,653 A | 7/1982 | Chauffe |
| 4,343,651 A | 8/1982 | Yazu et al. |
| 4,354,559 A | 10/1982 | Johnson |
| 4,373,581 A | 2/1983 | Toellner |
| 4,394,170 A | 7/1983 | Sawaoka et al. |
| 4,396,062 A | 8/1983 | Iskander |
| 4,412,585 A | 11/1983 | Bouck |
| 4,413,642 A | 11/1983 | Smith et al. |
| 4,449,585 A | 5/1984 | Bridges et al. |
| 4,457,365 A | 7/1984 | Kasevich et al. |
| 4,470,459 A | 9/1984 | Copland |
| 4,476,926 A | 10/1984 | Bridges et al. |
| 4,484,627 A | 11/1984 | Perkins |
| 4,485,868 A | 12/1984 | Sresty et al. |
| 4,485,869 A | 12/1984 | Sresty et al. |
| 4,487,257 A | 12/1984 | Dauphine |
| 4,495,990 A | 1/1985 | Titus et al. |
| 4,498,535 A | 2/1985 | Bridges |
| 4,499,948 A | 2/1985 | Perkins |
| 4,508,168 A | 4/1985 | Heeren |
| 4,513,815 A | 4/1985 | Rundell et al. |
| 4,524,826 A | 6/1985 | Savage |
| 4,524,827 A | 6/1985 | Bridges et al. |
| 4,545,435 A | 10/1985 | Bridges et al. |
| 4,553,592 A | 11/1985 | Looney et al. |
| 4,557,327 A | 12/1985 | Kinley et al. |
| 4,576,231 A | 3/1986 | Dowling et al. |
| 4,583,589 A | 4/1986 | Kasevich |
| 4,592,423 A | 6/1986 | Savage et al. |
| 4,612,988 A | 9/1986 | Segalman |
| 4,620,593 A | 11/1986 | Haagensen |
| 4,636,934 A | 1/1987 | Schwendemann |
| 4,660,636 A | 4/1987 | Rundell et al. |
| 4,705,108 A | 11/1987 | Little et al. |
| 4,817,711 A | 4/1989 | Jearnbey |
| 5,012,863 A | 5/1991 | Springer |
| 5,018,580 A | 5/1991 | Skipper |
| 5,037,704 A | 8/1991 | Nakai et al. |
| 5,055,180 A | 10/1991 | Klaila |
| 5,068,819 A | 11/1991 | Misra et al. |
| 5,070,952 A | 12/1991 | Neff |
| 5,074,355 A | 12/1991 | Lennon |
| 5,082,054 A | 1/1992 | Kiamanesh |
| 5,092,056 A | 3/1992 | Deaton |
| 5,107,705 A | 4/1992 | Wraight et al. |
| 5,107,931 A | 4/1992 | Valka et al. |
| 5,228,518 A | 7/1993 | Wilson et al. |
| 5,236,039 A | 8/1993 | Edelstein et al. |
| 5,278,550 A | 1/1994 | Rhein-Knudsen et al. |
| 5,388,648 A | 2/1995 | Jordan, Jr. |
| 5,490,598 A | 2/1996 | Adams |
| 5,501,248 A | 3/1996 | Kiest, Jr. |
| 5,690,826 A | 11/1997 | Cravello |
| 5,803,666 A | 9/1998 | Keller |
| 5,813,480 A | 9/1998 | Zaleski, Jr. et al. |
| 5,853,049 A | 12/1998 | Keller |
| 5,890,540 A | 4/1999 | Pia et al. |
| 5,899,274 A | 5/1999 | Frauenfeld et al. |
| 5,947,213 A | 9/1999 | Angle |
| 5,955,666 A | 9/1999 | Mullins |
| 5,958,236 A | 9/1999 | Bakula |
| RE36,362 E | 11/1999 | Jackson |
| 6,012,526 A | 1/2000 | Jennings et al. |
| 6,032,742 A | 3/2000 | Tomlin et al. |
| 6,041,860 A | 3/2000 | Nazzal et al. |
| 6,096,436 A | 8/2000 | Inspektor |
| 6,170,531 B1 | 1/2001 | Jung et al. |
| 6,173,795 B1 | 1/2001 | McGarian et al. |
| 6,189,611 B1 | 2/2001 | Kasevich |
| 6,254,844 B1 | 7/2001 | Takeuchi et al. |
| 6,268,726 B1 | 7/2001 | Prammer |
| 6,269,953 B1 | 8/2001 | Seyffert et al. |
| 6,290,068 B1 | 9/2001 | Adams et al. |
| 6,305,471 B1 | 10/2001 | Milloy |
| 6,325,216 B1 | 12/2001 | Seyffert et al. |
| 6,328,111 B1 | 12/2001 | Bearden et al. |
| 6,354,371 B1 | 3/2002 | O'Blanc |
| 6,371,302 B1 | 4/2002 | Adams et al. |
| 6,413,399 B1 | 7/2002 | Kasevich |
| 6,443,228 B1 | 9/2002 | Aronstam |
| 6,454,099 B1 | 9/2002 | Adams et al. |
| 6,510,947 B1 | 1/2003 | Schulte et al. |
| 6,534,980 B2 | 3/2003 | Toufaily et al. |
| 6,544,411 B2 | 4/2003 | Varandaraj |
| 6,561,269 B1 | 5/2003 | Brown et al. |
| 6,571,877 B1 | 6/2003 | Van Bilderbeek |
| 6,607,080 B2 | 8/2003 | Winkler et al. |
| 6,612,384 B1 | 9/2003 | Singh et al. |
| 6,623,850 B2 | 9/2003 | Kukino et al. |
| 6,629,610 B1 | 10/2003 | Adams et al. |
| 6,637,092 B1 | 10/2003 | Menzel |
| 6,678,616 B1 | 1/2004 | Winkler et al. |
| 6,722,504 B2 | 4/2004 | Schulte et al. |
| 6,761,230 B2 | 7/2004 | Cross et al. |
| 6,814,141 B2 | 11/2004 | Huh et al. |
| 6,827,145 B2 | 12/2004 | Fotland |
| 6,845,818 B2 | 1/2005 | Tutuncu et al. |
| 6,850,068 B2 | 2/2005 | Chernali et al. |

(56) References Cited

U.S. PATENT DOCUMENTS

| | | |
|---|---|---|
| 6,895,678 B2 | 5/2005 | Ash et al. |
| 6,912,177 B2 | 6/2005 | Smith |
| 6,971,265 B1 | 12/2005 | Sheppard et al. |
| 6,993,432 B2 | 1/2006 | Jenkins et al. |
| 7,000,777 B2 | 2/2006 | Adams et al. |
| 7,013,992 B2 | 3/2006 | Tessari et al. |
| 7,048,051 B2 | 5/2006 | McQueen |
| 7,063,155 B2 | 6/2006 | Ruttley |
| 7,091,460 B2 | 8/2006 | Kinzer |
| 7,109,457 B2 | 9/2006 | Kinzer |
| 7,115,847 B2 | 10/2006 | Kinzer |
| 7,216,767 B2 | 5/2007 | Schulte et al. |
| 7,312,428 B2 | 12/2007 | Kinzer |
| 7,322,776 B2 | 1/2008 | Webb et al. |
| 7,331,385 B2 | 2/2008 | Symington |
| 7,376,514 B2 | 5/2008 | Habashy et al. |
| 7,387,174 B2 | 6/2008 | Lurie |
| 7,445,041 B2 | 11/2008 | O'Brien |
| 7,455,117 B1 | 11/2008 | Hall et al. |
| 7,461,693 B2 | 12/2008 | Considine et al. |
| 7,484,561 B2 | 2/2009 | Bridges |
| 7,539,548 B2 | 5/2009 | Dhawan |
| 7,562,708 B2 | 7/2009 | Cogliandro et al. |
| 7,629,497 B2 | 12/2009 | Pringle |
| 7,631,691 B2 | 12/2009 | Symington et al. |
| 7,650,269 B2 | 1/2010 | Rodney |
| 7,677,673 B2 | 3/2010 | Tranquilla et al. |
| 7,730,625 B2 | 6/2010 | Blake |
| 7,951,482 B2 | 5/2011 | Ichinose et al. |
| 7,980,392 B2 | 7/2011 | Varco |
| 8,237,444 B2 | 8/2012 | Simon |
| 8,245,792 B2 | 8/2012 | Trinh et al. |
| 8,275,549 B2 | 9/2012 | Sabag et al. |
| 8,484,858 B2 | 7/2013 | Brannigan et al. |
| 8,511,404 B2 | 8/2013 | Rasheed |
| 8,526,171 B2 | 9/2013 | Wu et al. |
| 8,528,668 B2 | 9/2013 | Rasheed |
| 8,567,491 B2 | 10/2013 | Lurie |
| 8,794,062 B2 | 8/2014 | DiFoggio et al. |
| 8,884,624 B2 | 11/2014 | Homan et al. |
| 8,925,213 B2 | 1/2015 | Sallwasser |
| 8,960,215 B2 | 2/2015 | Cui et al. |
| 9,109,429 B2 | 8/2015 | Xu et al. |
| 9,217,323 B2 | 12/2015 | Clark |
| 9,222,350 B2 | 12/2015 | Vaughn et al. |
| 9,250,339 B2 | 2/2016 | Ramirez |
| 9,353,589 B2 | 5/2016 | Hekelaar |
| 9,394,782 B2 | 7/2016 | DiGiovanni et al. |
| 9,435,159 B2 | 9/2016 | Scott |
| 9,464,487 B1 | 10/2016 | Zurn |
| 9,470,059 B2 | 10/2016 | Zhou |
| 9,494,032 B2 | 11/2016 | Roberson et al. |
| 9,528,366 B2 | 12/2016 | Selman et al. |
| 9,562,987 B2 | 2/2017 | Guner et al. |
| 9,617,815 B2 | 4/2017 | Schwartze et al. |
| 9,651,468 B2 | 5/2017 | Rowe et al. |
| 9,664,011 B2 | 5/2017 | Kruspe et al. |
| 9,702,211 B2 | 7/2017 | Tinnen |
| 9,731,471 B2 | 8/2017 | Schaedler et al. |
| 9,739,141 B2 | 8/2017 | Zeng et al. |
| 9,912,918 B2 | 3/2018 | Samuel |
| 10,000,983 B2 | 6/2018 | Jackson et al. |
| 10,174,577 B2 | 1/2019 | Leuchtenberg et al. |
| 10,233,372 B2 | 3/2019 | Ramasamy et al. |
| 10,394,193 B2 | 8/2019 | Li et al. |
| 10,544,640 B2 | 1/2020 | Hekelaar et al. |
| 10,577,912 B2 | 3/2020 | Torrione |
| 10,796,424 B2 | 10/2020 | Parmeshwar et al. |
| 10,954,729 B2 | 3/2021 | Torrione |
| 2003/0159776 A1 | 8/2003 | Graham |
| 2003/0230526 A1 | 12/2003 | Okabayshi et al. |
| 2004/0182574 A1 | 9/2004 | Sarmad et al. |
| 2004/0256103 A1 | 12/2004 | Batarseh |
| 2005/0092523 A1 | 5/2005 | McCaskill et al. |
| 2005/0259512 A1 | 11/2005 | Mandal |
| 2006/0016592 A1 | 1/2006 | Wu |
| 2006/0106541 A1 | 5/2006 | Hassan et al. |
| 2006/0144620 A1 | 7/2006 | Cooper |
| 2006/0185843 A1 | 8/2006 | Smith |
| 2006/0249307 A1 | 11/2006 | Ritter |
| 2007/0131591 A1 | 6/2007 | Pringle |
| 2007/0137852 A1 | 6/2007 | Considine et al. |
| 2007/0175633 A1 | 8/2007 | Kosmala |
| 2007/0187089 A1 | 8/2007 | Bridges |
| 2007/0204994 A1 | 9/2007 | Wimmersperg |
| 2007/0289736 A1 | 12/2007 | Kearl et al. |
| 2008/0007421 A1 | 1/2008 | Liu et al. |
| 2008/0047337 A1 | 2/2008 | Chemali et al. |
| 2008/0173480 A1 | 7/2008 | Annaiyappa et al. |
| 2008/0190822 A1 | 8/2008 | Young |
| 2008/0308282 A1 | 12/2008 | Standridge et al. |
| 2009/0153354 A1 | 6/2009 | Daussin |
| 2009/0164125 A1 | 6/2009 | Bordakov et al. |
| 2009/0178809 A1 | 7/2009 | Jeffryes et al. |
| 2009/0259446 A1 | 10/2009 | Zhang et al. |
| 2010/0089583 A1 | 4/2010 | Xu et al. |
| 2010/0276209 A1 | 11/2010 | Yong et al. |
| 2010/0282511 A1 | 11/2010 | Maranuk |
| 2011/0011576 A1 | 1/2011 | Cavender et al. |
| 2011/0120732 A1 | 5/2011 | Lurie |
| 2012/0012319 A1 | 1/2012 | Dennis |
| 2012/0111578 A1 | 5/2012 | Tverlid |
| 2012/0132418 A1 | 5/2012 | McClung |
| 2012/0152543 A1 | 6/2012 | Davis |
| 2012/0173196 A1 | 7/2012 | Miszewski |
| 2012/0186817 A1 | 7/2012 | Gibson et al. |
| 2012/0222854 A1 | 9/2012 | McClung, III |
| 2012/0227983 A1 | 9/2012 | Lymberopoulous et al. |
| 2012/0273187 A1 | 11/2012 | Hall |
| 2013/0008653 A1 | 1/2013 | Schultz et al. |
| 2013/0008671 A1 | 1/2013 | Booth |
| 2013/0025943 A1 | 1/2013 | Kumar |
| 2013/0076525 A1 | 3/2013 | Vu et al. |
| 2013/0125642 A1 | 5/2013 | Parfitt |
| 2013/0126164 A1 | 5/2013 | Sweatman et al. |
| 2013/0146359 A1 | 6/2013 | Koederitz |
| 2013/0213637 A1 | 8/2013 | Kearl |
| 2013/0255936 A1 | 10/2013 | Statoilydro et al. |
| 2014/0083771 A1 | 3/2014 | Clark |
| 2014/0183143 A1 | 7/2014 | Cady et al. |
| 2014/0231075 A1 | 8/2014 | Springett et al. |
| 2014/0231147 A1 | 8/2014 | Bozso et al. |
| 2014/0238658 A1 | 8/2014 | Wilson et al. |
| 2014/0246235 A1 | 9/2014 | Yao |
| 2014/0251894 A1 | 9/2014 | Larson et al. |
| 2014/0278111 A1 | 9/2014 | Gerrie et al. |
| 2014/0291023 A1 | 10/2014 | Edbury |
| 2014/0333754 A1 | 11/2014 | Graves et al. |
| 2014/0360778 A1 | 12/2014 | Batarseh |
| 2014/0375468 A1 | 12/2014 | Wilkinson et al. |
| 2015/0020908 A1 | 1/2015 | Warren |
| 2015/0021240 A1 | 1/2015 | Wardell et al. |
| 2015/0083422 A1 | 3/2015 | Pritchard |
| 2015/0091737 A1 | 4/2015 | Richardson et al. |
| 2015/0101864 A1 | 4/2015 | May |
| 2015/0159467 A1 | 6/2015 | Hartman et al. |
| 2015/0211362 A1 | 7/2015 | Rogers |
| 2015/0267500 A1 | 9/2015 | Dogen |
| 2015/0290878 A1 | 10/2015 | Houben et al. |
| 2015/0300151 A1 | 10/2015 | Mohaghegh |
| 2016/0004929 A1* | 1/2016 | Varghese ............ H04N 19/136 |
| | | 382/103 |
| 2016/0053572 A1 | 2/2016 | Snoswell |
| 2016/0053604 A1 | 2/2016 | Abbassian |
| 2016/0076357 A1 | 3/2016 | Hbaieb |
| 2016/0115783 A1 | 4/2016 | Zeng et al. |
| 2016/0119591 A1 | 4/2016 | Samuel |
| 2016/0130928 A1 | 5/2016 | Torrione |
| 2016/0153240 A1 | 6/2016 | Braga et al. |
| 2016/0160106 A1 | 6/2016 | Jamison et al. |
| 2016/0237810 A1 | 8/2016 | Beaman et al. |
| 2016/0247316 A1 | 8/2016 | Whalley et al. |
| 2016/0356125 A1 | 12/2016 | Bello et al. |
| 2017/0056928 A1 | 3/2017 | Torrione |

(56) References Cited

U.S. PATENT DOCUMENTS

| | | | |
|---|---|---|---|
| 2017/0058620 A1 | 3/2017 | Torrione | |
| 2017/0089153 A1 | 3/2017 | Teodorescu | |
| 2017/0161885 A1* | 6/2017 | Parmeshwar | G06T 7/0004 |
| 2017/0234104 A1 | 8/2017 | James | |
| 2017/0292376 A1 | 10/2017 | Kumar et al. | |
| 2017/0314335 A1 | 11/2017 | Kosonde et al. | |
| 2017/0328196 A1 | 11/2017 | Shi et al. | |
| 2017/0328197 A1 | 11/2017 | Shi et al. | |
| 2017/0342776 A1 | 11/2017 | Bullock et al. | |
| 2017/0350201 A1 | 12/2017 | Shi et al. | |
| 2017/0350241 A1 | 12/2017 | Shi | |
| 2018/0010030 A1 | 1/2018 | Ramasamy et al. | |
| 2018/0010419 A1 | 1/2018 | Livescu et al. | |
| 2018/0171772 A1 | 6/2018 | Rodney | |
| 2018/0187498 A1 | 7/2018 | Soto et al. | |
| 2018/0265416 A1 | 9/2018 | Ishida et al. | |
| 2018/0326679 A1 | 11/2018 | Weisenberg et al. | |
| 2019/0049054 A1 | 2/2019 | Gunnarsson et al. | |
| 2019/0101872 A1 | 4/2019 | Li | |
| 2019/0227499 A1 | 7/2019 | Li et al. | |
| 2019/0257180 A1 | 8/2019 | Kriesels et al. | |
| 2019/0368287 A1 | 12/2019 | Shekhar et al. | |
| 2020/0032638 A1 | 1/2020 | Ezzeddine | |
| 2020/0126386 A1* | 4/2020 | Michalopulos | G06T 17/00 |
| 2020/0157929 A1 | 5/2020 | Torrione | |
| 2021/0180417 A1 | 6/2021 | Shekhar et al. | |
| 2022/0018241 A1* | 1/2022 | Affleck | E21B 47/00 |
| 2022/0136344 A1* | 5/2022 | Mora | G01V 8/00 175/48 |
| 2022/0307370 A1* | 9/2022 | Rowe | E21B 49/005 |
| 2022/0381132 A1* | 12/2022 | Badis | E21B 47/002 |
| 2024/0263553 A1* | 8/2024 | Holt | E21B 44/06 |

FOREIGN PATENT DOCUMENTS

| | | |
|---|---|---|
| CN | 200989202 | 12/2007 |
| CN | 203232293 | 10/2013 |
| CN | 204627586 | 9/2015 |
| CN | 107208478 | 9/2017 |
| CN | 107462222 | 12/2017 |
| CN | 110571475 | 12/2019 |
| EP | 2317068 | 5/2011 |
| EP | 2574722 | 4/2013 |
| EP | 2737173 | 6/2014 |
| GB | 2124855 | 2/1984 |
| GB | 2357305 | 6/2001 |
| GB | 2399515 | 9/2004 |
| GB | 2422125 | 7/2006 |
| GB | 2532967 | 6/2016 |
| JP | 2009067609 | 4/2009 |
| JP | 4275896 | 6/2009 |
| JP | 5013156 | 8/2012 |
| NO | 343139 | 11/2018 |
| NO | 20161842 | 5/2019 |
| RU | 2282708 | 8/2006 |
| WO | WO 1995035429 | 12/1995 |
| WO | WO 2000025942 | 5/2000 |
| WO | WO 2000031374 | 6/2000 |
| WO | WO 2001042622 | 6/2001 |
| WO | WO 2002068793 | 9/2002 |
| WO | WO 2004042185 | 5/2004 |
| WO | WO 2007049026 | 5/2007 |
| WO | WO 2007070305 | 6/2007 |
| WO | WO 2008146017 | 12/2008 |
| WO | WO 2009020889 | 2/2009 |
| WO | WO 2009113895 | 9/2009 |
| WO | WO 2010105177 | 9/2010 |
| WO | WO 2011038170 | 3/2011 |
| WO | WO 2011042622 | 6/2011 |
| WO | WO 2012007407 | 1/2012 |
| WO | WO 2013016095 | 1/2013 |
| WO | WO 2013148510 | 10/2013 |
| WO | WO 2015095155 | 6/2015 |
| WO | WO 2016178005 | 11/2016 |
| WO | WO 2017011078 | 1/2017 |
| WO | WO 2017132297 | 8/2017 |
| WO | WO 2018169991 | 9/2018 |
| WO | WO 2019040091 | 2/2019 |
| WO | WO 2019055240 | 3/2019 |
| WO | WO 2019089926 | 5/2019 |
| WO | WO 2019108931 | 6/2019 |
| WO | WO 2019117857 | 6/2019 |
| WO | WO 2019160859 | 8/2019 |
| WO | WO 2019169067 | 9/2019 |
| WO | WO 2019236288 | 12/2019 |
| WO | WO 2019246263 | 12/2019 |

OTHER PUBLICATIONS

"IADC Dull Grading for PDC Drill Bits," Beste Bit, SPE/IADC 23939, 1992, 52 pages.

Aires et al., "Optical flow using color information: preliminary results," Proceedings of the 2008 ACM Symposium on Applied Computing, Mar. 2008, 1607-1611.

Akersolutions, "Aker MH CCTC Improving Safety," Aker Solutions, Jan. 2008, 12 pages.

Anwar et al., "Fog computing: an overview of big IoT data analytics," Wireless communications and mobile computing, May 2018, 2018: 1-22.

Artymiuk et al., "The new drilling control and monitoring system," Acta Montanistica Slovaca, Sep. 2004, 9(3): 145-151.

Ashby et al., "Coiled Tubing Conveyed Video Camera and Multi-Arm Caliper Liner Damage Diagnostics Post Plug and Perf Frac," Society of Petroleum Engineers, SPE-172622-MS, Mar. 2015, p. 12.

Bilal et al., "Potentials, trends, and prospects in edge technologies: Fog, cloudlet, mobile edge, and micro data centers," Computer Networks, Elsevier, Oct. 2017, 130: 94-120.

Carpenter, "Advancing Deepwater Kick Detection", JPT, vol. 68, Issue 5, May 2016, 2 pages.

Commer et al., "New advances in three-dimensional controlled-source electromagnetic inversion," Geophys. J. Int., 2008, 172: 513-535.

Dickens et al., "An LED array-based light induced fluorescence sensor for real-time process and field monitoring," Sensors and Actuators B: Chemical, Elsevier, Apr. 2011, 158(1): 35-42.

Dong et al., "Dual Substitution and Spark Plasma Sintering to Improve Ionic Conductivity of Garnet $Li_7La_3Zr_2O_{12}$," Nanomaterials, 9, 721, 2019, 10 pages.

Downholediagnostic.com [online] "Acoustic Fluid Level Surveys," retrieved from URL <https://www.downholediagnostic.com/fluid-level> retrieved on Mar. 27, 2020, available on or before 2018, 13 pages.

Du et al., "Classifying Cutting vol. at Shale Shakers in Real-Time Via Video Streaming Using Deep-Learning Techniques," SPE Drilling & Completion, Sep. 2020, 35(03):317-328.

Edition.cnn.com [online], "Revolutionary gel is five times stronger than steel," retrieved from URL <https://edition.cnn.com/style/article/hydrogel-steel-japan/index.html>, retrieved on Apr. 2, 2020, available on or before Jul. 16, 2017, 6 pages.

Gemmeke and Ruiter, "3D ultrasound computer tomography for medical imagining," Nuclear Instruments and Methods in Physics Research A 580, Oct. 1, 2007, 9 pages.

Guilherme et al., "Petroleum well drilling monitoring through cutting image analysis and artificial intelligence techniques," Engineering Applications of Artificial Intelligence, Feb. 2011, 201-207.

Halliburton, "Drill Bits and Services Solutions Catalogs," retrieved from URL: <https://www.halliburton.com/content/dam/ps/public/sdbs/sdbs_contents/Books_and_Catalogs/web/DBS-Solution.pdf> on Sep. 26, 2019. Copyright 2014, 64 pages.

Hopkin, "Factor Affecting Cuttings Removal during Rotary Drilling," Journal of Petroleum Technology 19.06, Jun. 1967, 8 pages.

Ji et al., "Submicron Sized Nb Doped Lithium Garnet for High Ionic Conductivity Solid Electrolyte and Performance of All Solid-State Lithium Battery," doi:10.20944/preprints201912.0307.v1, Dec. 2019, 10 pages.

(56)            References Cited

OTHER PUBLICATIONS

Johnson et al., "Advanced Deepwater Kick Detection," IADC/SPE 167990, presented at the 2014 IADC/SPE Drilling Conference and Exhibition, Mar. 4-6, 2014, 10 pages.

Johnson, "Design and Testing of a Laboratory Ultrasonic Data Acquisition System for Tomography" Thesis for the degree of Master of Science in Mining and Minerals Engineering, Virginia Polytechnic Institute and State University, Dec. 2, 2004, 108 pages.

King et al., "Atomic layer deposition of TiO2 films on particles in a fluidized bed reactor," Power Technology, vol. 183, Issue 3, Apr. 2008, 8 pages.

Li et al., 3D Printed Hybrid Electrodes for Lithium-ion Batteries, Missouri University of Science and Technology, Washington State University; ECS Transactions, 77 (11) 1209-1218 (2017), 11 pages.

Liu et al., "Flow visualization and measurement in flow field of a torque converter," Mechanic automation and control Engineering, Second International Conference on IEEE, Jul. 15, 2011, 1329-1331.

Liu et al., "Superstrong micro-grained polycrystalline diamond compact through work hardening under high pressure," Appl. Phys. Lett. Feb. 2018, 112: 6 pages.

Luo et al., "Simple Charts to Determine Hole Cleaning Requirements in Deviated Wells," IADC/SPE 27486, SPE/IADC Drilling Conference, Society of Petroleum Engineers, Feb. 15-18, 1994, 7 pages.

Maurer, "The Perfect Cleaning Theory of Rotary Drilling," Journal of Petroleum Technology 14.11, 1962, 5 pages.

nature.com [online], "Mechanical Behavior of a Soft Hydrogel Reinforced with Three-Dimensional Printed Microfibre Scaffolds," retrieved from URL <https://www.nature.com/articles/s41598-018-19502-y>, retrieved on Apr. 2, 2020, available on or before Jan. 19, 2018, 47 pages.

Nuth, "Smart oil field distributed computing," The Industrial Ethernet Book, Nov. 2014, 85(14):1-3.

Olver, "Compact Antenna Test Ranges," Seventh International Conference on Antennas and Propagation IEEE , Apr. 15-18, 1991, 10 pages.

Paiaman et al., "Effect of Drilling Fluid Properties on Rate Penetration," Nafta vol. 60, No. 3, 2009, 6 pages.

Parini et al., "Chapter 3: Antenna measurements," in Theory and Practice of Modern Antenna Range Measurements, IET editorial, 2014, 30 pages.

petrowiki.org [online], "Kicks," Petrowiki, available on or before Jun. 26, 2015, retrieved on Jan. 24, 2018, retrieved from URL <https://petrowiki.org/Kicks>, 6 pages.

Ranjbar, "Cutting Transport in Inclined and Horizontal Wellbore," University of Stavanger, Faculty of Science and Technology, Master's Thesis, Jul. 6, 2010, 137 pages.

Rasi, "Hold Cleaning in Large, High-Angle Wellbores," SPE/IADC Drilling Conference, Society of Petroleum Engineers, Feb. 15-18, 1994, 12 pages.

rigzone.com [online], "How does Well Control Work?" Rigzone, available on or before 1999, retrieved on Jan. 24, 2019, retrieved from URL <https://www.rigzone.com/training/insight.asp?insight_id-304&c_id>, 5 pages.

Robinson and Morgan, "Effect of Hole Cleaning on Drilling Rate Performance," Paper Aade-04-Df-Ho-42, AADE 2004 Drilling Fluids Conference, Houston, Texas, Apr. 6-7, 2004, 7 pages.

Robinson, "Economic Consequences of Poor Solids and Control," AADE 2006 Fluids Conference and Houston, Texas, Apr. 11-12, 2006, 9 pages.

Ruiter et al., "3D ultrasound computer tomography of the breast: A new era?" European Journal of Radiology 81S1, Sep. 2012, 2 pages.

sageoiltools.com [online] "Fluid Level & Dynamometer Instruments for Analysis due Optimization of Oil and Gas Wells," retrieved from URL <http://www.sageoiltools.com/>, retrieved on Mar. 27, 2020, available on or before 2019, 3 pages.

Schlumberger, "First Rigless ESP Retrieval and Replacement with Slickline, Offshore Congo: Zeitecs Shuttle System Eliminates Need to Mobilize a Workover Rig," slb.com/zeitecs, 2016, 1 page.

Schlumberger, "The Lifting Business," Offshore Engineer, Mar. 2017, 1 page.

Schlumberger, "Zeitecs Shuttle System Decreases ESP Replacement Time by 87%: Customer ESP riglessly retrieved in less than 2 days on coiled tubing," slb.com/zeitecs, 2015, 1 page.

Schlumberger, "Zeitecs Shuttle System Reduces Deferred Production Even Before ESP is Commissioned, Offshore Africa: Third Party ESP developed fault during installation and was retrieved on rods, enabling operator to continue running tubing without waiting on replacement," slb.com/zeitecs, 2016, 2 pages.

Schlumberger, "Zeitecs Shuttle: Rigless ESP replacement system," Brochure, 8 pages.

Schlumberger, "Zeitecs Shuttle: Rigless ESP replacement system," Schlumberger, 2017, 2 pages.

Sifferman et al., "Drilling cutting transport in full scale vertical annuli," Journal of Petroleum Technology 26.11, 48th Annual Fall Meeting of the Society of Petroleum Engineers of AIME, Las Vegas, Sep. 30-Oct. 3, 1973, 12 pages.

slb.com' [online] "Technical Paper: ESP Retrievable Technology: A Solution to Enhance ESP Production While Minimizing Costs," SPE 156189 presented in 2012, retrieved from URL <http://www.slb.com/resources/technical_papers/artificial_lift/156189.aspx>, retrieved on Nov. 2, 2018, 1 pages.

slb.com' [online], "Zeitecs Shuttle Rigless ESP Replacement System," retrieved from URL <http://www.slb.com/services/production/artificial_lift/submersible/zeitecs-shuttle.aspx?t=3>, available on or before May 31, 2017, retrieved on Nov. 2, 2018, 3 pages.

Sulzer Metco, "An Introduction to Thermal Spray," Issue 4, 2013, 24 pages.

Tobenna, "Hole Cleaning Hydraulics," Universitetet o Stavanger, Faculty of Science and Technology, Master's Thesis, Jun. 15, 2010, 75 pages.

Wei et al., "The Fabrication of All-Solid-State Lithium-Ion Batteries via Spark Plasma Sintering," Metals, 7, 372, 2017, 9 pages.

wikipedia.org [online] "Optical Flowmeters," retrieved from URL <https://en.wikipedia.org/wiki/Flow_measurement#Optical_flowmeters>, retrieved on Mar. 27, 2020, available on or before Jan. 2020, 1 page.

wikipedia.org [online] "Ultrasonic Flow Meter," retrieved from URL <https://en.wikipedia.org/wiki/Ultrasonic_flow_meter> retrieved on Mar. 27, 2020, available on or before Sep. 2019, 3 pages.

wikipedia.org [online], "Surface roughness," retrieved from URL <https://en.wikipedia.org/wiki/Surface_roughness> retrieved on Apr. 2, 2020, available on or before Oct. 2017, 6 pages.

Williams and Bruce, "Carrying Capacity of Drilling Muds," Journal of Petroleum Technology, 3.04, vol. 192, 1951, 10 pages.

Xia et al., "A Cutting Concentration Model of a Vertical Wellbore Annulus in Deep-water Drilling Operation and its Application," Applied Mechanics and Materials, vol. 101-102, Sep. 27, 2011, 5 pages.

Xue et al., "Spark plasma sintering plus heat-treatment of Ta-doped Li7La3Zr2O12 solid electrolyte and its ionic conductivity," Mater. Res. Express 7 (2020) 025518, 8 pages.

Zhan et al. "Effect of β-to-α Phase Transformation on the Microstructural Development and Mechanical Properties of Fine-Grained Silicon Carbide Ceramics." Journal of the American Ceramic Society 84.5, May 2001, 6 pages.

Zhan et al. "Single-wall carbon nanotubes as attractive toughening agents in alumina-based nanocomposites." Nature Materials 2.1, Jan. 2003, 6 pages.

Zhan et al., "Atomic Layer Deposition on Bulk Quantities of Surfactant Modified Single-Walled Carbon Nanotubes," Journal of American Ceramic Society, vol. 91, Issue 3, Mar. 2008, 5 pages.

Zhang et al, "Increasing Polypropylene High Temperature Stability by Blending Polypropylene-Bonded Hindered Phenol Antioxidant," Macromolecules, 51(5), pp. 1927-1936, 2018, 10 pages.

Zhu et al., "Spark Plasma Sintering of Lithium Aluminum Germanium Phosphate Solid Electrolyte and its Electrochemical Properties," University of British Columbia; Nanomaterials, 9, 1086, 2019, 10 pages.

(56) References Cited

OTHER PUBLICATIONS

International Search Report and Written Opinion in International Appln. No. PCT/US2023/026335, mailed Aug. 29, 2023, 13 pages.

* cited by examiner

SYSTEM AND METHOD FOR AUTOMATED DRILL CUTTING MONITORING

TECHNICAL FIELD

This disclosure relates to wellbore, particularly to drilling wellbores.

BACKGROUND

Hydrocarbons trapped in subsurface reservoirs can be raised to the surface of the Earth (that is, produced) through wellbores formed from the surface to the subsurface reservoirs. Wellbore drilling systems are used to drill wellbores through a subterranean zone (for example, a formation, a portion of a formation or multiple formations) to the subsurface reservoir. At a high level, the wellbore drilling system includes a drill bit connected to an end of a drill string. The drill string is rotated and weight is applied on the drill bit to drill through the subterranean zone. Wellbore drilling fluid (also known as drilling mud) is flowed in a downhole direction through the drill string. The drilling fluid exits the drill bit through ports defined in the drill bit and flows in an uphole direction through an annulus defined by an outer surface of the drill string and an inner wall of the wellbore. As the drilling fluid flows towards the surface, it carries any cuttings and debris released into the wellbore due to and during the drilling. The cuttings and debris are released from the subterranean zone as the drill bit breaks the rock while penetrating the subterranean zone. When mixed with the drilling fluid, the cuttings and debris form a solid slurry that flows to the surface. At the surface, the cuttings and debris are filtered and the wellbore drilling fluid can be recirculated into the wellbore to continue drilling. The cuttings and debris carried to the surface by the drilling fluid provide useful information, among other things, about the wellbore being formed and the drilling process.

SUMMARY

This specification describes technologies relating to systems and method for automated well cutting monitoring.

Certain aspects of the subject matter described here can be implemented as a system that includes a digital imaging device and a computer system operatively coupled to the digital imaging device. The digital imaging device is mounted to a non-vibrating member of a shale shaker of a wellbore drilling assembly. The shale shaker is positioned at a surface of the Earth adjacent a wellbore and configured to receive a solid slurry that includes a mixture of wellbore drilling mud and solid objects found in the wellbore while drilling the wellbore through a subterranean zone. The solid objects include drill cuttings. The digital imaging device is oriented to face a portion of the shale shaker that receives the solid slurry. The digital imaging device is configured to capture digital images of the solid objects while the solid slurry is received by the shale shaker. The computer system includes one or more processors, and a computer-readable medium storing instructions executable by the one or more processors to perform operations. The operations include receiving the images captured by the digital imaging device. By implementing image processing techniques on the images, the computer system determines a space occupied by the solid objects on the shale shaker. The computer system determines wellbore conditions using the space occupied by the solid objects on the shale shaker.

An aspect including one or more of any of the other aspects includes the following features. To determine the space occupied by the solid objects on the shale shaker by implementing the image processing techniques on the images, the computer system determines a ratio of space not occupied by the solid objects on the shale shaker to the space occupied by the solid objects on the shale shaker.

An aspect including one or more of any of the other aspects includes the following features. To determine the wellbore conditions using the space occupied by the solid objects on the shale shaker, the computer system, in a first time instant, determines that the ratio is greater than a first threshold ratio. In response, the computer system determines that the wellbore conditions comprise an overpressured formation.

An aspect including one or more of any of the other aspects includes the following features. To determine the wellbore conditions using the space occupied by the solid objects on the shale shaker, the computer system, in a second time instant different from the first time instant, determines that the ratio is lesser than a second threshold ratio, which is lesser than the first threshold ratio. In response, the computer system determines that the wellbore conditions include a stuck pipe event.

An aspect including one or more of any of the other aspects includes the following features. By implementing the image processing techniques on the images, the computer system determines a speed at which the solid objects are deposited onto the shale shaker.

An aspect including one or more of any of the other aspects includes the following features. To determine the wellbore conditions using the speed at which the solid objects are deposited on the shale shaker, the computer system, in a third time instant, determines that the speed is lesser than a first speed threshold. In response, the computer system determines that the wellbore conditions include overweight wellbore drilling mud.

An aspect including one or more of any of the other aspects includes the following features. To determine the wellbore conditions using the speed at which the solid objects are deposited onto the shale shaker, the computer system, in a fourth time instant different from the second time instant, determines that the speed is greater than a second speed threshold, which is greater than the first speed threshold. In response, the computer system determines that the wellbore conditions include underweight wellbore drilling mud.

An aspect including one or more of any of the other aspects includes the following features. By implementing the image processing techniques on the images, the computer system determines a size of the solid objects deposited onto the shale shaker.

An aspect including one or more of any of the other aspects includes the following features. To determine the wellbore conditions using the size of the solid objects deposited onto the shale shaker, the computer system, in a fifth time instant, determines that the size is greater than a size threshold. In response, the computer system determines a presence of cavings or a formation failure.

An aspect including one or more of any of the other aspects includes the following features. The system includes an alarm system connected to the computer system. The computer system is configured to transmit a signal to the alarm system in response to determining the wellbore conditions. The alarm system is configured to transmit an alarm in response to receiving the signal from the computer system.

An aspect including one or more of any of the other aspects includes the following features. The images include digital video.

An aspect including one or more of any of the other aspects includes the following features. To implement the image processing techniques on the images, the computer system is configured to perform operations including normalizing a low-frequency component of the digital video using running average method.

Certain aspects of the subject matter described here can be implemented as methods, e.g., computer-implemented methods, described here.

Certain aspects of the subject matter described here can be implemented as a non-transitory computer-readable medium storing instructions executable by one or more processors to perform the methods described here.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Wellbore drilling involves breaking rock in a subterranean zone to form and deepen a wellbore and carrying the broken rock (drill cuttings) to the wellbore surface by wellbore mud flowed through the wellbore. The cuttings concentration and classification at the surface provide engineers, geologists and drilling operators with valuable insights about the drilling process including hole cleaning efficiency, characteristics of rock formations that are useful for different applications to optimize drilling performance, and identification of formation changes to reduce non-productive times (NPT) to name a few.

One way to determine the efficiency of pumping, sweeping and drilling operations is to observe the characteristic behavior of drill cuttings in the wellbore. Solid particles emerging from the well can be identified as planned (e.g., cutting) or unplanned (e.g., cavings). Planned or wanted solids include drilled solids of a certain geometry (often dependent on the drill bit design) when drilling open hole rock or other materials such as cement, metals or composites, when drilling other downhole elements such as casing windows, plugs or cement shoes. Unplanned solids include rock of unwanted geometry, signifying a failed or worn drill bit, geo-mechanical problems such as collapsing formations (such as a shale) or poor fluid and cutting transportation.

Figure 1:
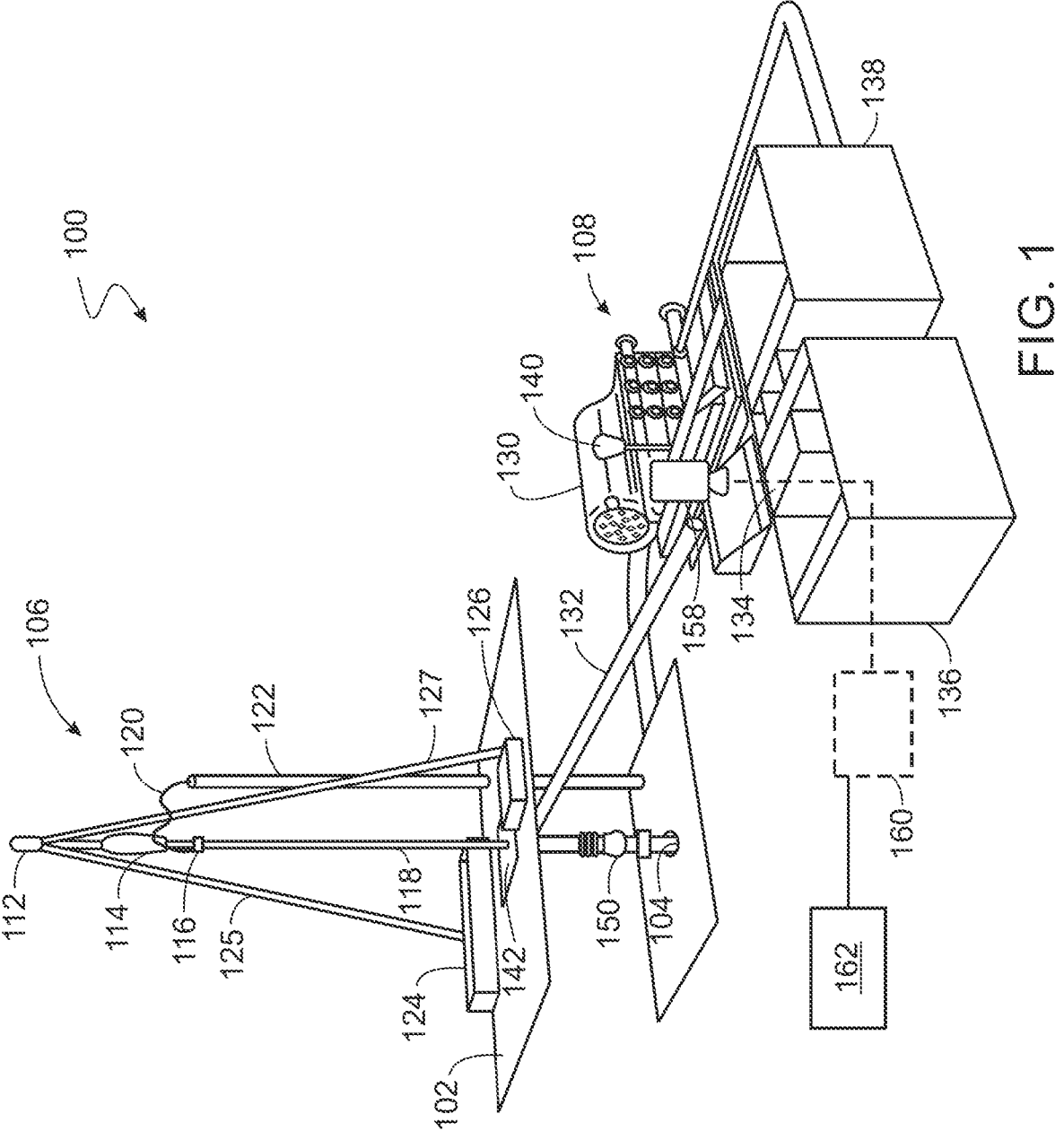
FIG. 1 is a schematic diagram of a wellbore drilling assembly 100 with real-time solid object monitoring.

This disclosure describes the use of image capture devices (e.g., cameras) to record shale shakers as well as computational models for the automatic analysis and characterization of wanted or unwanted observed solids, in real-time. For example, during wellbore drilling, one or more cameras are positioned adjacent the shale shaker to capture images (e.g., videos) of cuttings that flow to the shale shaker. Image processing is performed on the captured images to enhance image quality and to minimize effects of low-frequency components on the video frame. A region of interest on the shale shaker is identified, and a ratio of filled space versus empty space on the shale shaker is determined. If the ratio is greater than a first threshold, then that indicates an overpressured formation. In contrast, if the ratio is lesser than a second threshold, then that indicates a stuck pipe event. In addition, a speed at which the cuttings move is determined. If the speed is lesser than a third threshold, then that indicates that the drilling mud may be too heavy. If the speed is greater than a fourth threshold, then that indicates that the mud may be too light. Further, cutting sizes are compared with a fifth threshold. If the sizes are larger than the fifth threshold, then that may indicate a presence of cavings and/or borehole failure. Alerts are transmitted based on the results of each comparison, and the drilling operator can adjust wellbore operations based on the alerts FIG. 1 is a schematic diagram of a wellbore drilling assembly 100 with real-time solid object monitoring. The wellbore can extend from the surface through the Earth to one or more subterranean zones of interest. The wellbore drilling assembly 100 includes a drill floor 102 positioned above the surface, a wellhead 104, a drill string assembly 106 supported by the rig structure, a fluid circulation system 108 to filter used drilling fluid from the wellbore and provide clean drilling fluid to the drill string assembly 106, and a monitoring system including a digital image capturing device 158 and an onsite computer system 160 (described in more detail later) to monitor in real time solid objects that flow from within the wellbore to the surface, specifically, onto the shale shaker 134. For example, the wellbore drilling assembly 100 of FIG. 1 is shown as a drill rig capable of performing a drilling operation with the wellbore drilling assembly 100 supporting the drill string assembly 106 over a wellbore. The wellhead 104 can be used to support casing or other wellbore components or equipment into the wellbore.

The derrick or mast is a support framework mounted on the drill floor 102 and positioned over the wellbore to support the components of the drill string assembly 106 during drilling operations. A crown block 112 forms a longitudinally-fixed top of the derrick, and connects to a travelling block 114 with a drilling line including a set of wire ropes or cables. The crown block 112 and the travelling block 114 support the drill string assembly 106 via a swivel 116, a kelly 118, or a top drive system (not shown).

Longitudinal movement of the travelling block 114 relative to the crown block 112 of the drill string assembly 106 acts to move the drill string assembly 106 longitudinally upward and downward. The swivel 116, connected to and hung by the travelling block 114 and a rotary hook, allows free rotation of the drill string assembly 106 and provides a connection to a kelly hose 120, which is a hose that flows drilling fluid from a drilling fluid supply of the circulation system 108 to the drill string assembly 106. A standpipe 122 mounted on the drill floor 102 guides at least a portion of the kelly hose 120 to a location proximate to the drill string assembly 106. The kelly 118 is a hexagonal device suspended from the swivel 116 and connected to a longitudinal top of the drill string assembly 106, and the kelly 118 turns with the drill string assembly 106 as the rotary table 142 of the drill string assembly turns. The techniques described in this disclosure can be implemented with a top drive system or with the kelly 118.

In the wellbore drilling assembly 100 of FIG. 1, the drill string assembly 106 is made up of drill pipes with a drill bit (not shown) at a longitudinally bottom end of the drill string. The drill pipe can include hollow steel piping, and the drill bit can include cutting tools, such as blades, dics, rollers, cutters, or a combination of these, to cut into the formation and form the wellbore. The drill bit rotates and penetrates through rock formations below the surface under the combined effect of axial load and rotation of the drill string assembly 106. In some implementations, the kelly 118 and swivel 116 can be replaced by a top drive that allows the drill string assembly 106 to spin and drill. The wellhead assembly 104 can also include a drawworks 124 and a deadline anchor 126, where the drawworks 124 includes a winch that acts as a hoisting system to reel the drilling line in and out to raise and lower the drill string assembly 106 by a fast line 125. The deadline anchor 126 fixes the drilling line opposite the drawworks 124 by a deadline 127, and can measure the suspended load (or hook load) on the rotary hook. The weight on bit (WOB) can be measured when the drill bit is at the bottom the wellbore. The wellhead assembly 104 also includes a blowout preventer 150 positioned at the surface 101 of the wellbore and below (but often connected to) the drill floor 102. The blowout preventer 150 acts to prevent wellbore blowouts caused by formation fluid entering the wellbore, displacing drilling fluid, and flowing to the surface at a pressure greater than atmospheric pressure. The blowout preventer 150 can close around (and in some instances, through) the drill string assembly 106 and seal off the space between the drill string and the wellbore wall. The blowout preventer 150 is described in more detail later.

During a drilling operation of the well, the circulation system 108 circulates drilling mud from the wellbore to the drill string assembly 106, filters used drilling mud from the wellbore, and provides clean drilling mud to the drill string assembly 106. The example circulation system 108 includes a fluid pump 130 that fluidly connects to and provides drilling mud to drill string assembly 106 via the kelly hose 120 and the standpipe 122. The circulation system 108 also includes a flow-out line 132, a shale shaker 134, a settling pit 136, and a suction pit 138. In a drilling operation, the circulation system 108 pumps drilling mud from the surface, through the drill string assembly 106, out the drill bit and back up the annulus of the wellbore, where the annulus is the space between the drill pipe and the formation or casing. The hydrostatic pressure from the drilling mud is intended to be greater than the formation pressures to prevent formation fluids from entering the annulus and flowing to the surface and lesser than the mechanical strength of the formation, as a greater pressure may fracture the formation, thereby creating a path for the drilling muds to go into the formation. Apart from wellbore control, drilling muds can also cool the drill bit and lift rock cuttings from the drilled formation up the annulus and to the surface to be filtered out and treated before it is pumped down the drill string assembly 106 again. The drilling mud returns in the annulus with rock cuttings and flows out to the flow-out line 132, which connects to and provides the fluid to the shale shaker 134. The flow line is an inclined pipe that directs the drilling mud from the annulus to the shale shaker 134. The shale shaker 134 includes a mesh-like surface to separate the coarse rock cuttings from the drilling mud, and finer rock cuttings and drilling mud then go through the settling pit 136 to the suction pit 136. The circulation system 108 includes a mud hopper 140 into which materials (for example, to provide dispersion, rapid hydration, and uniform mixing) can be introduced to the circulation system 108. The fluid pump 130 cycles the drilling mud up the standpipe 122 through the swivel 116 and back into the drill string assembly 106 to go back into the wellbore.

The example wellhead assembly 104 can take a variety of forms and include a number of different components. For example, the wellhead assembly 104 can include additional or different components than the example shown in FIG. 1. Similarly, the circulation system 108 can include additional or different components than the example shown in FIG. 1.

During the drilling operation, solid objects emerge from the wellbore. The solid objects can include drill cuttings, each of which is a rock separated from the formation in response to the drill bit contacting the formation while drilling the wellbore. When drilling open (that is, uncased) wellbores, the drill cuttings can be expected to have a certain geometry that corresponds to the drill bit design. When drilling other downhole elements such as casing windows, plugs or cement shoes in wellbore operations different from wellbore formation, drill cuttings can include cement, elastomers, metals or composites.

The digital imaging device 158 and the computer system 160 together form a solid object monitoring system that can track each solid object (or liquid) as it emerges from the wellbore and passes through the shale shaker 134. In some implementations, the digital imaging device 158 (for example, a smart camera, an image sensor, vision sensor network or similar digital imaging device) can capture digital images as each solid object is deposited onto the shale shaker 134. The computer system 160 can receive the images captured by the digital imaging device 158 after the solid object has been deposited onto the shale shaker 134. By implementing image processing techniques on the images, the computer system 160 can determine a volume of solid objects deposited onto the shale shaker 134. Using the volume, the computer system 160 can determine a space occupied by the solid objects on the shale shaker 134. Using the space occupied by the solid objects on the shale shaker 134, the computer system 160 can determine wellbore conditions.

In some implementations, the computer system 160 can implement other image processing techniques on the images to determine other types of wellbore conditions. The output of implementing the other image processing techniques includes determining a speed at which the solid objects are deposited onto the shale shaker 134 and determining a size of each solid object (or a group of solid objects) deposited onto the shale shaker 134. In some implementations, the computer system 160 can determine the wellbore conditions using solely the output of each image processing technique. In some implementations, the computer system 160 can combine the output of different image processing techniques to determine wellbore conditions that otherwise could not be determined using the output of just one image processing technique.

Implementations are disclosed in the context of the digital imaging device 158 mounted to the shale shaker 134. Alternatively or in addition, the digital imaging device 158 can be mounted on other components of the wellbore drilling assembly, for example, the centrifuge, de-sander, de-silter or other components past which the solid objects flowing out the wellbore pass. In some implementations, the digital imaging device 158 can be mounted elsewhere on the drilling rig site, for example, on a pole installed onto the drilling rig structure or onto or into the ground around the rig structure that effectively hoists the digital imaging device 158 to a birds eye view above the solids control equipment. In any such component, the digital imaging device 158 is mounted to a non-vibrating component that does not vibrate during operation so that the digital imaging device 158 can capture vibration-free images. In some implementations, vibration dampeners can be mounted to a component and the digital imaging device 158 can be mounted to any component whose vibrations have been dampened. In some implementations, the digital imaging device 158 can implement vibration control or shake reduction features to capture vibration- or shake-free images even if mounted on a vibrating structure of a wellbore drilling assembly component. In some implementations, vibration dampeners can be mounted to a component and shake reduction features can be implemented in the digital imaging device 150. In some implementations, image distortions due to vibration or shaking can be removed during image processing.

Figure 2A:
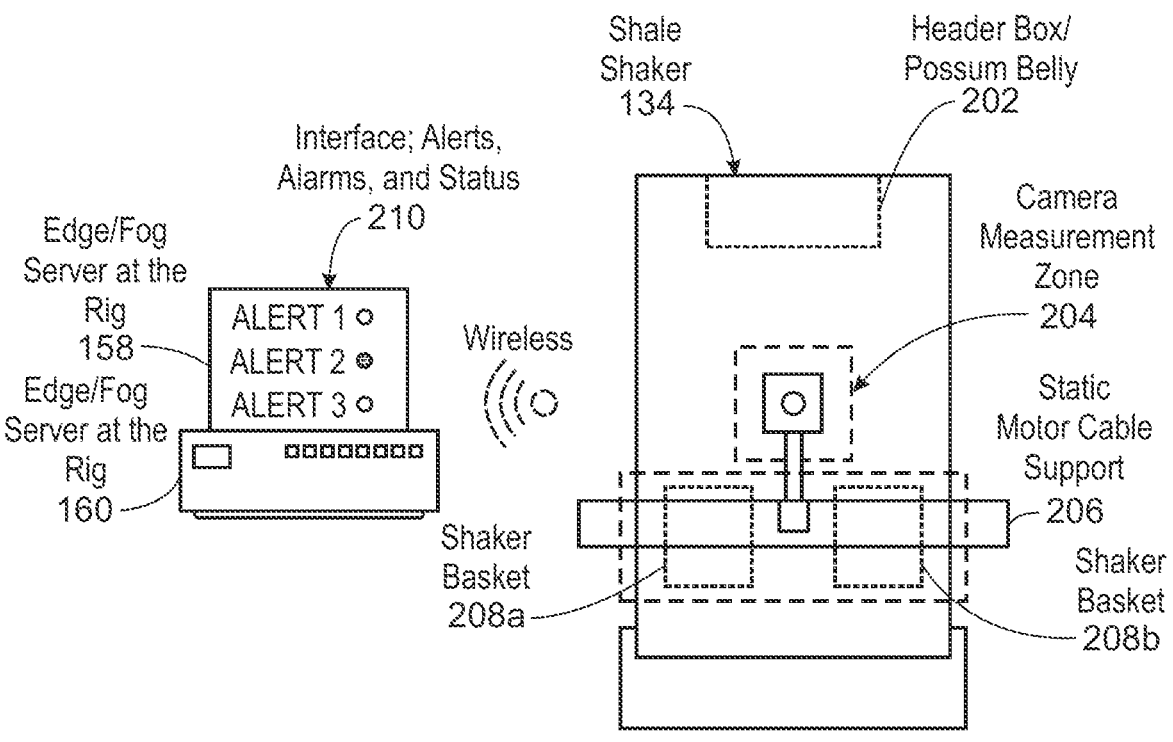
FIGS. 2A and 2B are schematic diagrams of a solid object monitoring system that is attached to the shale shaker 134.
Figure 2B:
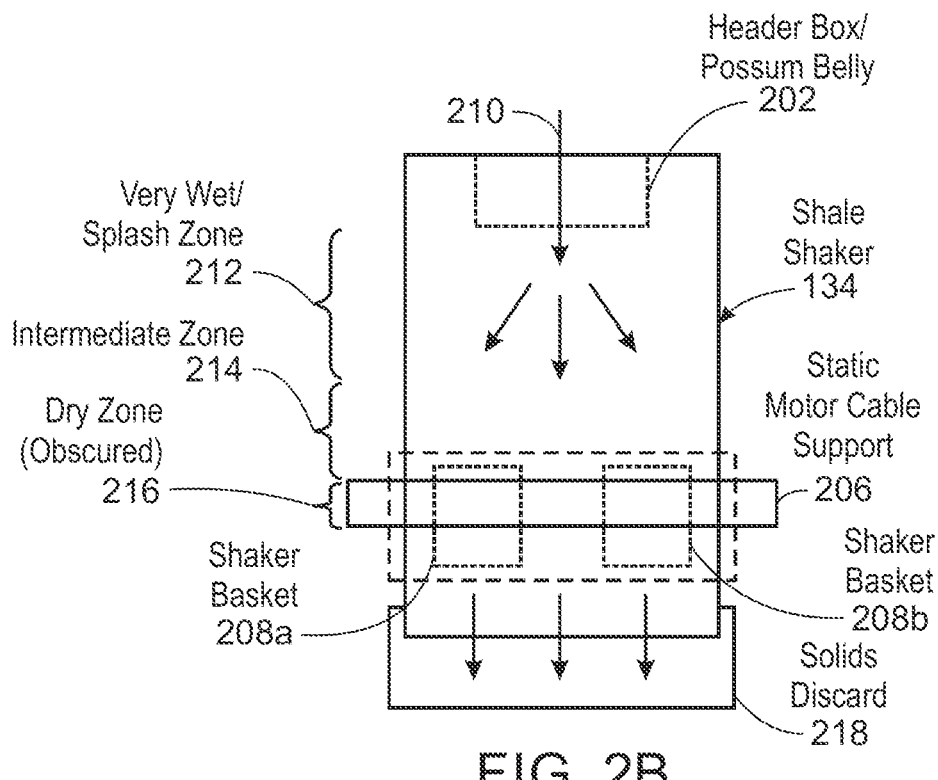

FIGS. 2A and 2B are schematic diagrams of a solid object monitoring system that is attached to the shale shaker 134. FIG. 2A shows that the shale shaker 134 includes a header box/possum belly 202 through which a solid slurry that includes a mixture of the solid objects and the wellbore drilling mud enter the shale shaker 134. Specifically, the solid slurry lands on a shaking screen and is carried downstream of the shale shaker 134 by a vibration of the shaking screen operated by shaker basket motors 208a, 208b. The shale shaker 134 includes a static motor cable support member 206 (for example, a swing arm or other static, non-vibrating member) which spans a width of the shaking screen and that carries cabling or wiring to power the motors 208a, 208b. In some implementations, an image capture zone 204 (sometimes called a camera measurement zone) is defined by the support member 206. The digital imaging device 158 is mounted on and directly attached to the support member 206. The digital imaging device 158 can include a smart, waterproof, high resolution, wireless camera or any other image or vision sensor such as infrared sensor, gamma ray sensor, computerized tomography (CT) scanner, or X-ray sensor, to name a few. The digital imaging device 158 is oriented such that its view finder or screen of the device 158 faces the solid slurry. In particular, the view finder or screen is capable of capturing a plan view of the shaking screen and of the solid objects moved by the shaking screen. The digital imaging device 158 can have a field of view that spans an entire width of the shaking screen so as to image an entirety of the solid slurry carried by the shaking screen. The field of view can also span a length segment of the shaking screen on which multiple solid objects are carried.

FIG. 2B shows different length segments of the moving tray or the mesh or sieve of the shale shaker 134. In particular, the length segment nearest the header box/possum belly 202 can be a very wet or splash zone 212 in which the solid slurry is the most wet, that is, has the largest concentration of drilling mud among all the length segments. The arrow 210 represents a direction of movement of the solid slurry as the shaking screen vibrates. The length segment downstream of the very wet or splash zone 212 is an intermediate zone 214 that is drier compared to the very wet or splash zone 212 because at least some but not all of the drilling mud has been drained from the solid slurry. The length segment downstream of the intermediate zone 214 is the dry zone in which the solid slurry is most dry, that is, has the least concentration of drilling mud among all the length segments. The dry zone 214 can be the length segment that is immediately upstream of the end of the shaking screen.

Most, if not all, of the drilling mud liquid has been drained from the slurry leaving only solid objects or mostly solid objects with very little drilling mud in the dry zone 214. The solid objects from which the drilling mud has been separated are discarded in the solids discard zone 218 downstream of the shale shaker screen. The drilling mud (and any fine solids, depending on the mesh size of the shale shaker screen) are gathered into a sump tank for further treatment and recycling for reuse in the wellbore drilling operation.

Returning to FIG. 2A, the digital imaging device 158 is operatively coupled to the computer system 160, for example, by wired or wireless operative coupling techniques. The computer system 160 includes a computer-readable medium (for example, a transitory or a non-transitory computer-readable medium) and one or more processors coupled to the computer-readable medium. The computer-readable medium stores computer instructions executable by the one or more processors to perform operations described in this disclosure. In some implementations, the computer system 160 can implement edge or fog computing hardware and software based on artificial intelligence models including machine learning and deep learning for image or video processing. Together, the digital imaging device 158 and the computer system 160 form an Internet of Things (IoT) platform to be used on a drilling rig and configured to implement a set of artificial intelligence models including machine learning (ML) and deep learning (DL) that serve as the foundation for enabling analysis of new sensors and data streams in real-time to provide advanced solutions for optimization of drilling operations.

In some wellbore drilling assemblies, multiple shale shakers can be implemented. In such instances, a single camera mounted to one of the shale shakers can be used for image capture. The computer system 160 can determine wellbore conditions using images captured by the single camera and extrapolate or calibrate the determination to the solid objects carried by other shale shakers. In some implementations, a respective camera can be mounted to each shale shaker, and all the shale shakers can transmit captured images to the computer system 160. In such implementations, the computer system 160 can determine wellbore conditions using images of solid objects carried by each individual shale shaker and also use solid objects carried by all the shale shakers.

Figures 3, 4:
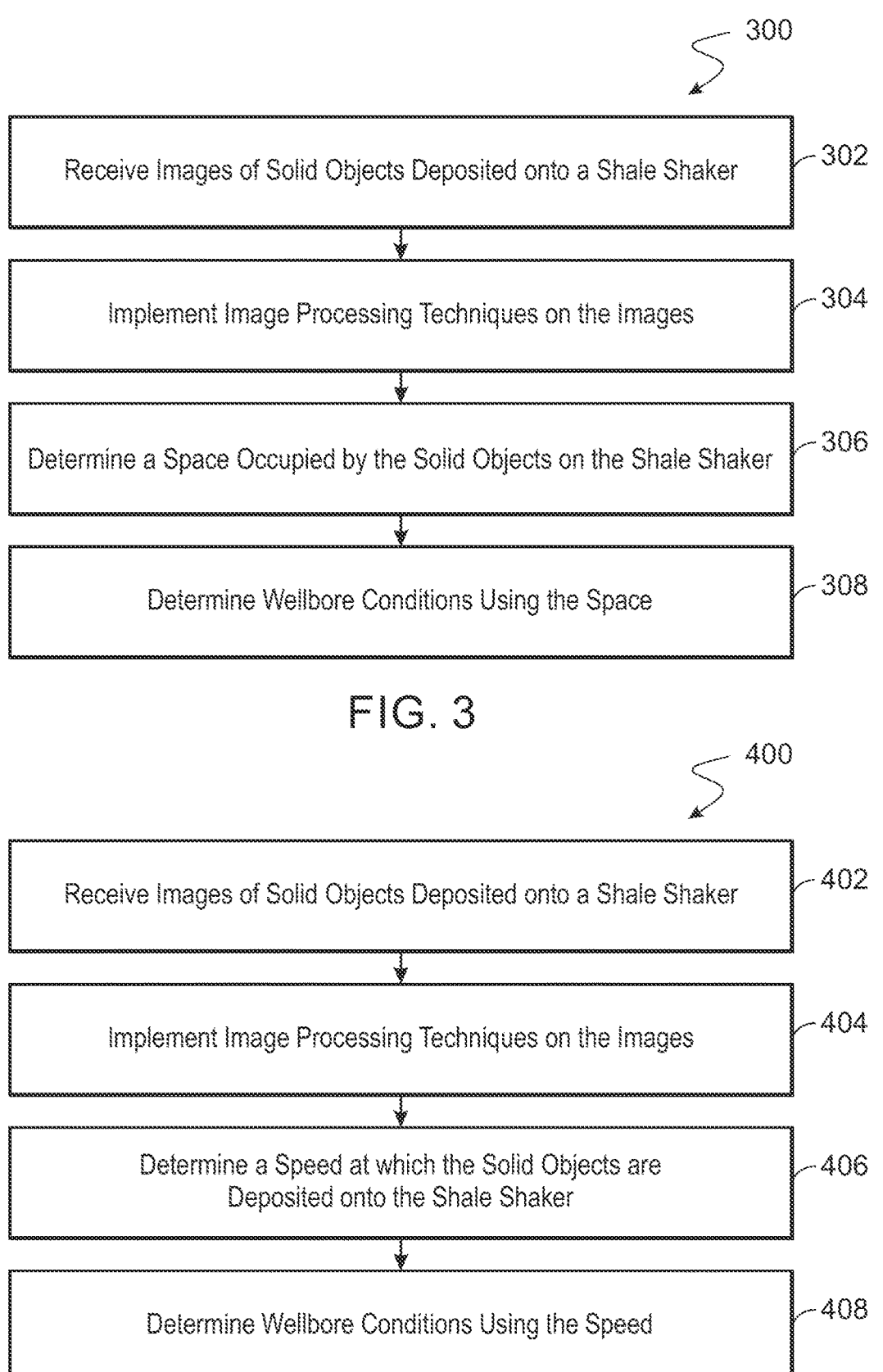
FIG. 3 is a flowchart of an example of a process for solid object monitoring.
FIG. 4 is a flowchart of an example of a process for solid object monitoring.

FIG. 3 is a flowchart of an example of a process 300 for solid object monitoring. In some implementations, the process 300 can be implemented by the computer system 160. At 302, the computer system 160 receives images captured by the digital imaging device 158 mounted to a non-vibrating member of the shale shaker 134. As described earlier, the digital imaging device 158 captures images (e.g., static digital images or digital video or a combination of them) of solid objects that result when the wellbore drilling assembly 100 drills through the subterranean zone. The digital imaging device 158 transmits the captured images to the computer system 160, for example, in real-time.

For the purposes of this disclosure, the terms "real-time," "real time," "realtime," "real (fast) time (RFT)," "near(ly) real-time (NRT)," "quasi real-time," or similar terms (as understood by one of ordinary skill in the art) mean that an action and a response are temporally proximate such that an individual perceives the action and the response occurring substantially simultaneously. For example, the time difference for a response to display (or for an initiation of a display) of data following the individual's action to access the data may be lesser than 1 ms, lesser than 1 sec., lesser than 5 secs., etc. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit (or a combination of these or other functions) the data.

At 304, image processing techniques are performed on the images. For example, the computer system 160 can implement the image processing techniques on the images. Where the received images include digital video, the computer system 160 processes the video frame-by-frame. The computer system 160 identifies two frames at a time. Specifically, the computer system 160 normalizes the background (i.e., the low frequency component of the video frame) with a running average method represented by Equation 1:

$$\text{Background}_k = \alpha \times \text{Background}_{k-1} + (1-\alpha) \times \text{blur(current frame)} \qquad \text{Eq. 1}$$

In Eq. 1, k is the current frame index, blur (current frame) is the current frame, blurred with low-pass filter (e.g., box filter or Gaussian filter), and parameter a (set between 0 and 1) controls the strength of background normalization: in case $\alpha=0$, no normalization occurs; when $\alpha=1$, the strongest normalization occurs, such that background is static, and it does not accumulate global changes at all. Normalized frame is computed according to the formula shown in Eq. 2.

$$\text{Normalized frame} = \text{(current frame} - \text{blur(current frame))} + \text{background}_k \qquad \text{Eq. 2}$$

This approach helps to reduce global light changes in the video: all details (high frequency component) is preserved, while changes in low frequency component are subsided.

At 306, a space occupied by the solid objects on the shale shaker 134 is determined using the processed images. For example, in real-time, the computer system 160 can perform a scan of each frame of the digital video (e.g., a pixel-by-pixel scan) to identify portions of each frame that are occupied by the solid objects and portions that are not. The computer system 160 can compare neighboring video frames to detect moving and stationary parts of video frames, and estimate the area of video frames occupied by moving parts in comparison with the full video frame. Using the results of the scan, the computer system 160 can determine a ratio of space not occupied by the solid objects on the shale shaker 134 to the space occupied by the solid objects on the shale shaker 134.

At 308, wellbore conditions are determined using the space identified in step 306. For example, the computer system 160 can store a predefined first threshold ratio. In real-time, the computer system 160 can determine that the ratio discussed with reference to step 306 is greater than the first threshold ratio. In response to determining that the ratio is greater than the first threshold ratio, the computer system 160 can determine that the wellbore conditions comprise an overpressured formation. An overpressure formation is one that experiences abnormally high subsurface pressure, one that exceeds hydrostatic pressure at a given depth. Such overpressure can occur in areas where burial of fluid-filled sediments is so rapid that pore fluids cannot escape causing the pressure of the pore fluids to increase as overburden increases. Drilling into overpressured formations can be hazardous because overpressured fluids escape rapidly. Consequently, the rate at which solid objects reach the surface during drilling increases. As more solid objects released when drilling into an overpressured formation reach the surface, more solid objects are deposited onto the shale shaker 134, and lesser space remains unoccupied on the shale shaker 134. Consequently, if the ratio of occupied to unoccupied space on the shale shaker 134 exceeds the first threshold ratio, that is an indication that the subterranean zone may be overpressured.

In some implementations, the computer system 160 can determine the ratio discussed with reference to step 306 in a first time instant. In a second time instant different from the first time instant (i.e., before or after the first time instant), the computer system 160 can receive different images from the digital imaging device 158 (e.g., different digital video) and determine the ratio discussed with reference to step 306 using the images received at the second time instant. The computer system 160 can store a predefined second threshold ratio, which is lesser than the first threshold ratio. In real-time, the computer system 160 can determine that the ratio determined using the images received at the second time instant is lesser than the second threshold ratio. In response to determining that the ratio is lesser than the second threshold ratio, the computer system 160 can determine that the wellbore condition includes a stuck pipe event. A stuck pipe is a portion of a tubing (e.g., a drillstring) lowered into the subterranean zone that cannot be rotated or moved vertically. In a stuck pipe event, the flow of the drilling mud and the solid objects to the surface is obstructed. Consequently, the rate at which solid objects reach the surface during drilling decreases. As fewer solid objects released during the stuck pipe event reach the surface, fewer solid objects are deposited onto the shale shaker 134, and more space remains unoccupied on the shale shaker 134. Consequently, if the ratio of occupied to unoccupied space on the shale shaker 134 is lesser than the second threshold ratio, that is an indication of a stuck pipe event.

FIG. 4 is a flowchart of an example of a process 400 for solid object monitoring. In some implementations, the process 400 can be implemented by the computer system 160. At 402, the computer system 160 can receive images (e.g., digital video) of solid objects deposited onto the shale shaker. For example, step 402 can be substantially similar to step 302 (FIG. 3). At 404, image processing techniques are performed on the images. For example, the computer system 160 can implement the image processing techniques on the images in substantially the same manner in which the computer system 160 implemented step 304 (FIG. 4).

At step 406, a speed at which the solid objects are deposited onto the shale shaker can be determined. For example, the computer system 160 can implement optical flow techniques to determine the speed. In computer vision, optical flow is a velocity field associated with image changes occurring between neighboring (i.e., consecutive) video frames. Optical flow estimation algorithm are based on brightness changes between two video frames, and compute displacement of objects occurring between neighboring frames. In case optical flow is computed between all consecutive video frames, it is possible to reconstruct the trajectory of motion of the solid objects captured on video. The optical flow estimation algorithm can implement video compression, analysis, object tracking and other techniques to process the digital video. By implementing optical flow estimation, the computer system 160 can analyze the digital video and determine the speed of the solid objects (in meters per second). To measure speed from video, the computer system 160 can estimate the travel distance (in pixels) of solid objects between consecutive video frames. The computer system 160 can convert distance in pixels to distance in millimeters using camera optical system parameters such as focusing distance and field of view (FOV). The computer system 160 can project this distance, which is measured on the image plane, orthogonal to the camera optical axes, on the surface of the shale shaker 134 using angle between screening surface and optical axes of camera. The computer system 160 can recompute the speed in meters per second using known frame rate of the digital imaging device 158.

At 408, wellbore conditions are determined using the speed determined in step 406. For example, the computer system 160 can store a predefined first speed threshold. In real-time, the computer system 160 can determine that the speed discussed with reference to step 406 is lesser than the first speed threshold. In response to determining that the speed is lesser than the first speed threshold, the computer system 160 can determine that the wellbore conditions comprise overweight wellbore drilling mud. Drilling mud weight controls hydrostatic pressure in a wellbore and prevents unwanted flow into the well. The weight of the mud also prevents collapse of casing and the open hole. Overweight drilling mud can cause lost circulation by propagating and filling fractures in the subterranean zone. It the drilling mud is overweight, then the flow rate of the drilling mud through the wellbore being formed can be lesser than an optimal flow rate if the drilling mud were of optimal weight. Consequently, a speed at which the solid objects are carried to the surface and deposited onto the shale shaker 134 decreases. Therefore, if the speed at which the solid objects are deposited onto the shale shaker 134 is lesser than the first speed threshold, that is an indication that the drilling mud may be overweight.

In some implementations, the computer system 160 can determine the speed discussed with reference to step 406 in a first time instant. In a second time instant different from the first time instant (i.e., before or after the first time instant), the computer system 160 can receive different images from the digital imaging device 158 (e.g., different digital video) and determine the speed discussed with reference to step 406 using the images received at the second time instant. The computer system 160 can store a predefined second speed threshold, which is greater than the first speed threshold. In real-time, the computer system 160 can determine that the speed determined using the images received at the second time instant, is greater than the second speed threshold. In response to determining that the speed is greater than the second speed threshold, the computer system 160 can determine that the drilling mud is underweight. Mud weight controls hydrostatic pressure in a wellbore and prevents unwanted flow into the well. Underweight mud can cause blow-out and significant increase of cuttings volume transported from the well.

Figure 5:
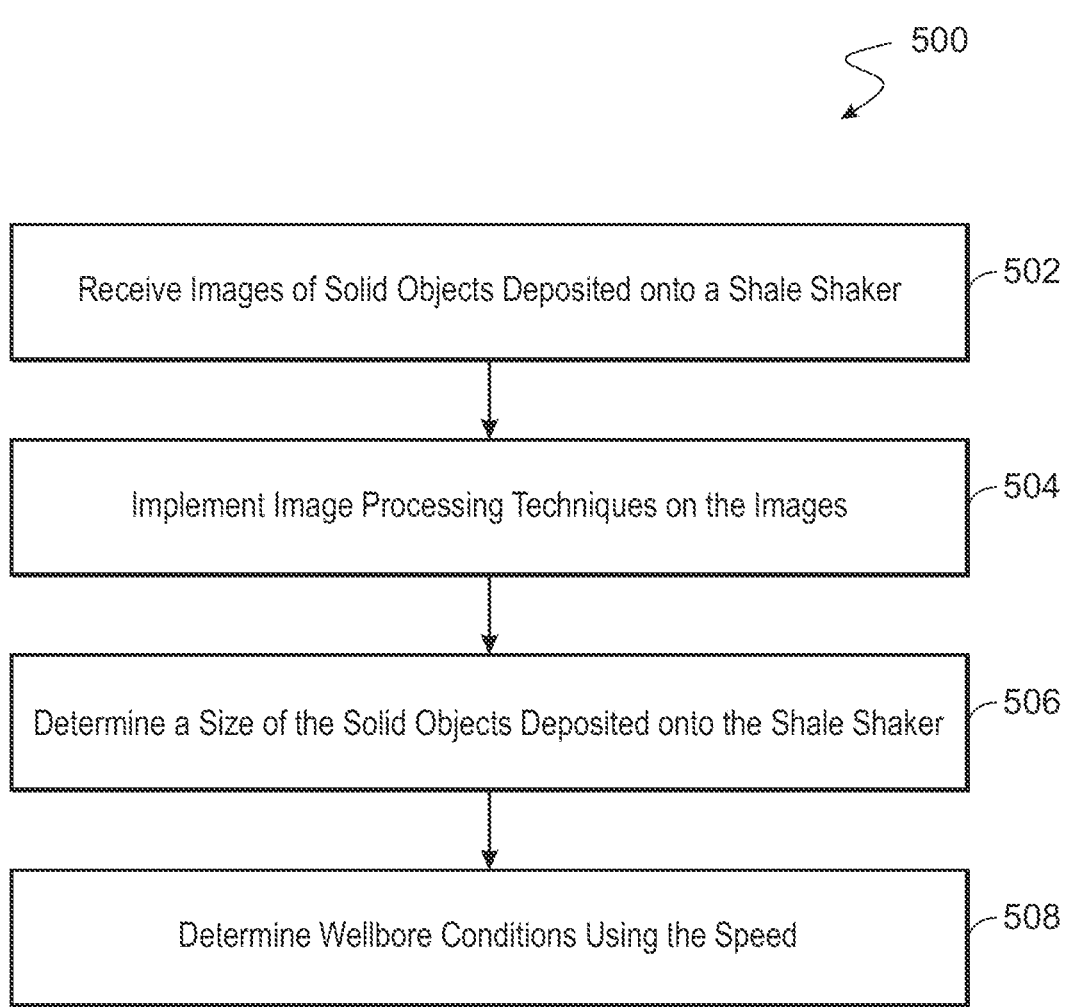
FIG. 5 is a flowchart of an example of a process for solid object monitoring.

FIG. 5 is a flowchart of an example of a process 500 for solid object monitoring. In some implementations, the process 500 can be implemented by the computer system 160. At 502, the computer system 160 can receive images (e.g., digital video) of solid objects deposited onto the shale shaker. For example, step 502 can be substantially similar to step 302 (FIG. 3). At 504, image processing techniques are performed on the images. For example, the computer system 160 can implement the image processing techniques on the images in substantially the same manner in which the computer system 160 implemented step 304 (FIG. 4).

At step 506, a of the solid objects deposited onto the shale shaker can be determined. For example, in real-time, the computer system 160 can perform a scan of each frame of the digital video (e.g., a pixel-by-pixel scan) to identify portions of each frame that are occupied by the solid objects and portions that are not. Using results of the scan, the computer system 160 can identify the solid objects in each frame. Then, the computer system 160 can determine a long axis and a short axis for each solid object from the image of the solid object. To do so, the computer system 160 can implement instances segmentation to segment out different parts of the video frame that show different solid objects. The computer system 160 can also analyze two-dimensional (2D) images of the solid objects to determine an object size. For example, using the long and short axes, the computer system 160 can determine a size distribution curve of the solid objects. It is expected that the solid objects will have a range of sizes. However, unusually large solid objects (i.e., solid objects having size that is 3-5 times larger than a solid object having an average size, as determined using the size distribution curve) can represent the presence of cavings or borehole failure.

At 508, wellbore conditions are determined using the size determined in step 506. For example, the computer system 160 can store a predefined first size threshold. In real-time, the computer system 160 can determine that the size discussed with reference to step 506 is greater than the first size threshold. In response to determining that the size is greater than the first size threshold, the computer system 160 can determine that the wellbore conditions comprise cavings or borehole failure.

In some implementations, the computer system 160 can be programmed to implement one or more or all of the processes 300, 400 or 500. Alternatively or in addition, the computer system 160 can be programmed to automatically perform each of the processes 300, 400 or 500, either in series or in parallel.

In some implementations, the determination of a wellbore condition can trigger an alarm, for example, in real-time. For example and returning to FIG. 1, the computer system 160 can be operatively coupled to an alarm system 162. The computer system 160 is configured to transmit a signal to the alarm system 162 in response to determining the wellbore conditions. The alarm system 162 is configured to transmit an alarm (e.g., an audible signal, a visual signal, a tactile signal, any other alarm signal that can be sensed or a combination of them) in response to receiving the signal from the computer system 160.

In some implementations, a wellbore operator, upon receiving or sensing the alarm from the alarm system 162, can manually adjust wellbore drilling operations or to account for existing conditions in the subterranean zone. Alternatively or in addition, the computer system 160 can not only transmit the alarm signal to the alarm system 162, but can also transmit signals to respective equipment of the wellbore drilling assembly 100 to adjust the wellbore drilling parameters to account for the wellbore conditions. For example, in response to determining a stuck pipe event, the computer system 160 can cause the wellbore pumps to cease operation so that the stuck pipe event can be addressed.

Thus, particular implementations of the subject matter have been described. Other implementations are within the scope of the following claims.

The invention claimed is:

1. A system comprising:
   a digital imaging device mounted to a non-vibrating member of a shale shaker of a wellbore drilling assembly, the shale shaker positioned at a surface of the Earth adjacent a wellbore and configured to receive a solid slurry comprising a mixture of wellbore drilling mud and solid objects found in the wellbore while drilling the wellbore through a subterranean zone, the solid objects comprising drill cuttings, the digital imaging device oriented to face a portion of the shale shaker that receives the solid slurry, the digital imaging device configured to capture digital images of the solid objects while the solid slurry is received by the shale shaker; and a computer system operatively coupled to the digital imaging device, the computer system comprising:

one or more processors; and a computer-readable medium storing instructions executable by the one or more processors to perform operations comprising:

receiving the images captured by the digital imaging device;

by implementing image processing techniques on the images, determining a ratio of space occupied by the solid objects on the shale shaker to empty space on the shale shaker; and determining wellbore conditions using the ratio.

2. The system of claim 1, wherein determining the wellbore conditions using the ratio comprises, in a first time instant:

determining that the ratio is greater than a first threshold ratio; and in response to determining that the ratio is greater than the first threshold ratio, determining that the wellbore conditions comprise an overpressured formation.

3. The system of claim 2, wherein determining the wellbore conditions using the ratio comprises, in a second time instant different from the first time instant:

determining that the ratio is lesser than a second threshold ratio, which is lesser than the first threshold ratio; and in response to determining that the ratio is lesser than the second threshold ratio, determining that the wellbore conditions comprise a stuck pipe event.

4. The system of claim 1, further comprising, by implementing the image processing techniques on the images, determining a speed at which the solid objects are deposited onto the shale shaker.

5. The system of claim 4, wherein determining the wellbore conditions using the speed at which the solid objects are deposited on the shale shaker comprises, in a third time instant:

determining that the speed is lesser than a first speed threshold; and in response to determining that the speed is lesser than the first speed threshold, determining that the wellbore conditions comprise overweight wellbore drilling mud.

6. The system of claim 5, wherein determining the wellbore conditions using the speed at which the solid objects are deposited onto the shale shaker comprises, in a fourth time instant different from the third time instant:

determining that the speed is greater than a second speed threshold, which is greater than the first speed threshold; and in response to determining that the speed is greater than the second speed threshold, determining that the wellbore conditions comprise underweight wellbore drilling mud.

7. The system of claim 1, further comprising, by implementing the image processing techniques on the images, determining a size of the solid objects deposited onto the shale shaker.

8. The system of claim 7, wherein determining the wellbore conditions using the size of the solid objects deposited onto the shale shaker comprises, in a fifth time instant:

determining that the size is greater than a size threshold; and in response to determining that the size is greater than the size threshold, determining that the wellbore conditions comprise a presence of cavings or a formation failure.

9. The system of claim 1, further comprising an alarm system connected to the computer system, wherein the computer system is configured to transmit a signal to the alarm system in response to determining the wellbore conditions, and wherein the alarm system is configured to transmit an alarm in response to receiving the signal from the computer system.

10. The system of claim 1, wherein the images comprise digital video.

11. The system of claim 10, wherein to implement the image processing techniques on the images, the computer system is configured to perform operations comprising normalizing a low-frequency component of the digital video using running average method.

12. A method comprising:

receiving, by one or more processors, images captured by a digital imaging device mounted to a non-vibrating member of a shale shaker of a wellbore drilling assembly, the shale shaker positioned at a surface of the Earth adjacent a wellbore and configured to receive a solid slurry comprising a mixture of wellbore drilling mud and solid objects found in the wellbore while drilling the wellbore through a subterranean zone, the solid objects comprising drill cuttings, the digital imaging device oriented to face a portion of the shale shaker that receives the solid slurry, the digital imaging device configured to capture digital images of the solid objects while the solid slurry is received by the shale shaker;

by implementing image processing techniques on the images:

determining a ratio of space occupied by the solid objects on the shale shaker to empty space on the shale shaker; and determining wellbore conditions using the space occupied by the ratio.

13. The method of claim 12, wherein determining the wellbore conditions using the ratio comprises, in a first time instant:

determining that the ratio is greater than a first threshold ratio; and in response to determining that the ratio is greater than the first threshold ratio, determining that the wellbore conditions comprise an overpressured formation.

14. The method of claim 13, wherein determining the wellbore conditions using the ratio comprises, in a second time instant different from the first time instant:

determining that the ratio is lesser than a second threshold ratio, which is lesser than the first threshold ratio; and in response to determining that the ratio is lesser than the second threshold ratio, determining that the wellbore conditions comprise a stuck pipe event.

15. The method of claim 12, further comprising, by implementing the image processing techniques on the images, determining a speed at which the solid objects are deposited onto the shale shaker.

16. A non-transitory computer-readable medium storing instructions executable by one or more processors to perform operations comprising:

receiving, by one or more processors, images captured by a digital imaging device mounted to a non-vibrating member of a shale shaker of a wellbore drilling assembly, the shale shaker positioned at a surface of the Earth adjacent a wellbore and configured to receive a solid slurry comprising a mixture of wellbore drilling mud and solid objects found in the wellbore while drilling the wellbore through a subterranean zone, the solid objects comprising drill cuttings, the digital imaging device oriented to face a portion of the shale shaker that receives the solid slurry, the digital imaging device configured to capture digital images of the solid objects while the solid slurry is received by the shale shaker; and by implementing image processing techniques on the images:

determining a ratio of space occupied by the solid objects on the shale shaker to empty space on the shale shaker, a speed at which the solid objects are deposited onto the shale shaker, and a size of the solid objects on the shale shaker; and determining wellbore conditions using the ratio, a speed at which the solid objects are deposited onto the shale shaker, and a size of the solid objects on the shale shaker.

17. The medium of claim 16, wherein determining the wellbore conditions using the speed at which the solid objects are deposited on the shale shaker comprises, in a first time instant:

determining that the speed is lesser than a first speed threshold; and in response to determining that the speed is lesser than the first speed threshold, determining that the wellbore conditions comprise overweight wellbore drilling mud.

18. The medium of claim 17, wherein determining the wellbore conditions using the speed at which the solid objects are deposited on the shale shaker comprises, in a second time instant different from the first time instant:

determining that the speed is greater than a second speed threshold, which is greater than the first speed threshold; and in response to determining that the speed is greater than the second speed threshold, determining that the wellbore conditions comprise underweight wellbore drilling mud.

* * * * *